United States Patent [19]

Hartwig

[11] Patent Number: 4,751,315

[45] Date of Patent: Jun. 14, 1988

[54] PROCESS FOR THE PREPARATION OF CLAUSENAMIDE

[75] Inventor: Wolfgang Hartwig, Wuppertal, Fed. Rep. of Germany

[73] Assignees: Bayer Aktiengesellschaft, Leverkusen, Fed. Rep. of Germany; Chinese Academy of Medical Sciences, Beijing, China

[21] Appl. No.: 91,623

[22] Filed: Sep. 1, 1987

Related U.S. Application Data

[62] Division of Ser. No. 915,309, Oct. 3, 1986.

[30] Foreign Application Priority Data

Oct. 18, 1985 [DE] Fed. Rep. of Germany ....... 3537075

[51] Int. Cl.⁴ ........................................... C07D 207/12
[52] U.S. Cl. .................................... 548/530; 548/539; 548/551
[58] Field of Search ......................... 548/551, 530, 539

[56] References Cited

U.S. PATENT DOCUMENTS 4,119,637 10/1978 Cale, Jr. ........................... 548/551 X Primary Examiner—Joseph Paul Brust
Attorney, Agent, or Firm—Sprung Horn Kramer & Woods

[57] ABSTRACT

A new synthetic route to clausenamide having the formula

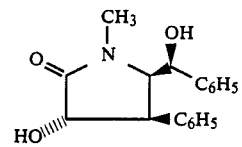

has been found. It has been found that a compound of the formula

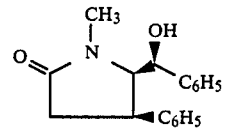

can be oxidized to provide the stereochemically correctly configured product, clausenamide. A number of new compounds useful in the total synthesis of clausenamide have also been found. These compounds have the general formula

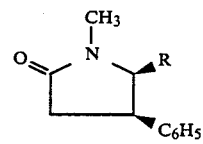

wherein R is

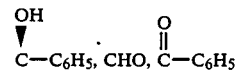

and $CH_2OH$.

4 Claims, No Drawings

PROCESS FOR THE PREPARATION OF CLAUSENAMIDE

This is a division of application Ser. No. 915,309, filed Oct. 3, 1986, now allowed.

The invention relates to a process for the preparation of (±)3(S*),4(R*),5(R*),7(S*)-3-hydroxy-5-α-hydroxybenzyl-1-methyl-4-phenyl-pyrrolidin-2-one (clausenamide).

It is known that *Rutaceae Clausena anicata* is used as a folk medicine in certain parts of Africa [J. Mester et al., Planta Medica 32, 81 (1977)]. It is also known that the crude extract of *Clausena indica Oliv.* has cardiovascular activity, and that two coumarin derivatives, clausmarin A and B, isolated from *Clausena pentaphalla* (Roxb.) by thin layer chromatography have spasmolytic activity [Dhan Prakash et al., J. Chem. Soc. Chem. Commun. 1978, 281]. In addition, the aqueous extract of leaves of *Clausena Lansium* (lour) Skeels is also regarded as an effective agent for protecting the liver in Chinese folk medicine and is employed against acute and chronic viral hepatitis. It has been possible to isolate (±)3(S*),4(R*),5(R*),7(S*)-3-hydroxy-5-α-hydroxybenzyl-1-methyl-4-phenylpyrrolidin-2-one (clausenamide) of the formula (I) from this extract as one of the main constituents.

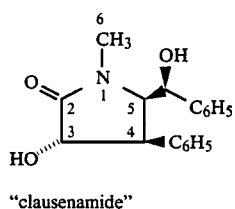

"clausenamide"

Clausenamide shows an antiamnesic action and an action affording protection from cerebral hypoxia in animal experiments. Since larger amounts are required for further pharmacological studies and, on the other hand, only 1.5 g of clausenamide are obtained from 4 kg of dried leaves by the expensive extraction process, it was necessary to provide a process for the chemical synthesis of clausenamide.

The present invention relates to a process for the preparation of (±)3(S*),4(R*),5(R*),7(S*)-3-hydroxy-5-α-hydroxy benzyl-1-methyl-4-phenyl-pyrrolidin-2-one (I), characterised in that (±)4(R*),5(R*),7(S*)-5-hydroxybenzyl-1-methyl-4-phenylpyrrolidin-2-one of the formula (II)

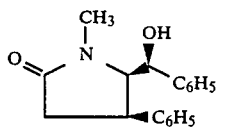

is oxidised in inert organic solvents in the presence of a base, if appropriate in the presence of an auxiliary.

It is to be described as decidedly surprising that exclusively the correctly configured $C_3$–$C_4$-transhydroxylation product (I) is formed in a good yield with the aid of the process according to the invention. The product is identical to the clausenamide obtained from a plant extract. In comparison with the extraction process, larger amounts can be provided in a shorter time and with less expenditure by the new process. In addition, the contamination of the clausenamide by other plant active compounds which can be removed only with difficulty is excluded.

The course of the reaction can be represented by the following equation:

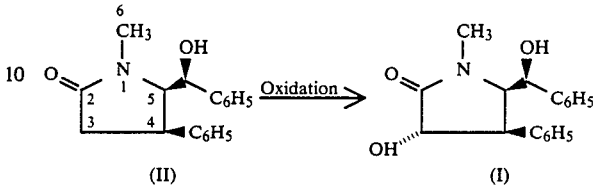

Oxidising agents which can be employed are organic or inorganic peroxo compounds, such as, for example, peroxoacetic acid, chloroperbenzoic acid or the molybdenum peroxide/pyridine complex, and in addition oxygen, ozone or oxygen transfer agents, such as, for example, 2-sulphonyloxaziridine.

Possible solvents are the customary inert organic solvents which do not change under the reaction conditions. These include, preferably, hydrocarbons, such as, for example, benzene, toluene, xylene, hexane, cyclohexane or petroleum fractions, ethers, such as diethyl ether, tetrahydrofuran or dioxane, alcohols, such as, for example, methanol, ethanol or propanol, halogenohydrocarbons, such as, for example, methylene chloride, chloroform, carbon tetrachloride or 1,2-dichloroethane, glacial acetic acid, acetonitrile or hexamethylphosphoric acid triamide. It is also possible to use mixtures of the solvents mentioned.

The customary bases for enolate formation can be used as the bases. These include, preferably, alkali metal alcoholates, alkali metal amides, alkali metal hydrides or organo-alkali metal compounds, such as, for example, sodium or potassium methanolate, sodium or potassium ethanolate, potassium tert.-butanolate, sodium hydride, sodium amide, lithium diisopropylamide, butyl-lithium or phenyl-lithium; tertiary amines, such as, for example, 1,5-diazabicyclo(4,3,0)non-5-ene or 1,8-diazabicyclo(5,4,0)undec-7-ene, can likewise be employed. Particularly preferred bases are lithium diisopropylamide, lithium hexamethylpiperidide and n-, sec.- or tert.-butyl- or phenyl-lithium.

The choice of base, solvent and, if appropriate, auxiliary depends on the oxidation method selected.

The auxiliaries used are, if appropriate, substances which are capable of reducing the hydroperoxide intermediate stages formed in situ, in particular when molybdenum peroxide pyridine or oxygen is used as the oxidising agent. Phosphites are preferably used for this, in particular trialkyl or triaryl phosphites, such as, for example, trimethyl phosphite, triethyl phosphite, tripropyl phosphite, triisopropyl phosphite, tributyl phosphite or triphenyl phosphite.

Oxidation with molybdenum peroxide/pyridine in hexamethylphosphoric acid triamide and with oxygen, in each case using phosphites, is particularly suitable. Especially good yields are obtained in oxidation with oxygen in a solvent, such as tetrahydrofuran or hexamethylphosphoric acid triamide, or if appropriate mixtures thereof, using triethyl phosphite. It has proved advantageous here to use lithium diisopropylamide or butyllithium as the base.

The reaction temperatures can be varied between −100° C. and +20° C. The reaction is preferably carried out between −78° C. and 0° C.

The hydroxylation by the process according to the invention can be carried out under normal pressure or under increased or reduced pressure. In general, it is carried out under normal pressure.

In carrying out the process according to the invention, 1 to 5, preferably 1 to 2.5, moles of base and 0.5 to 5, preferably 0.5 to 2, moles of the auxiliary are employed per mole of the starting compound.

The enolate of II is usually first prepared in the most suitable solvent with the aid of the base, and absolute oxygen is passed through the solution, with the addition of phosphite, until no further change is to be observed by thin layer chromatography. Working up of the reaction mixture is carried out in the customary manner known to the expert.

The starting compound of the formula (II) is new. It can be prepared by a process in which (±)(4R*),5(R*)-5-formyl-1-methyl-4-phenyl-pyrrolidin-2-one of the formula (III)

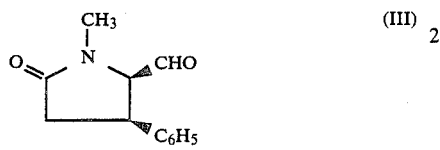

(III)

is reacted with organometallic compounds, such as Grignard reagents or titanium- or lithium-organyls, in suitable solvents in a temperature range from −20° C. to +50° C., preferably from −10° C. to +30° C., and, if appropriate, the product is epimerised on carbon atom 7.

Particularly suitable organometallic compound here are phenyl-magnesium bromide or chloride or phenyl-triisopropoxytitanium.

Suitable solvents are all the inert organic solvents which are usually employed in reactions with Grigard reagents or other organometallic reagents. These include, preferably, ethers, such as diethyl ether or tetrahydrofuran, if appropriate mixed with hexane.

The reaction can be carried out by a process analogous to processes which are known from the literature, such as are described, for example, by D. Seebach, B. Weidmann and L. Widler in "Modern Synthetic Methods 1983" page 217 et seq. (Verlag Salle und Sauerländer) or in Houben-Weyl's "Methoden der organischen Chemie" ("Methods of Organic Chemistry") Volume XIII/2a, page 289 et seq., page 302 et seq., or by N. L. Drake and G. B. Cooke in Organic Synthesis, Coll. Vol. II, 406 et seq. (1963).

Depending on the nature of the organometallic reagent used, the (±)4(R*),5(R*),7(R*)-5-α-hydroxybenzyl-1-methyl-4-phenyl-pyrrolidin-2-one R*-configurated on carbon atom 7, of the formula (IIa)

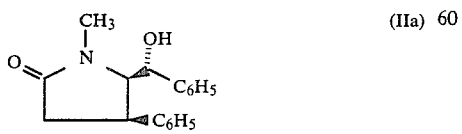

(IIa)

can first be formed, and is then epimerised by oxidation to (±)4(R*),5(R*)-5-benzoyl-1-methyl-4-phenylpyrrolidin-2-one (IV)

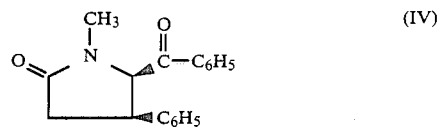

(IV)

and subsequent reduction of IV to give the 7-S*-configurated product (II).

The oxidation of IIa to IV is carried out by a process analogous to known processes with dimethylsulphoxide as the oxidising agent, with the addition of anhydrides, in particular trifluoroacetic anhydride, in suitable organic solvents, in particular in halogenohydrocarbons, such as, for example, methylene chloride or chloroform, or hydrocarbons, such as benzene, toluene, xylene or hexane, or ethers, such as diethyl ether, dioxane or tetrahydrofuran, or a mixtures of the solvents mentioned, such as is described, for example, by S. L. Huang, K. Omura and D. Swern in Synthesis 1980, 297.

The reduction of IV to II can be carried out with the customary reducing agents. Metal hydrides and complex metal hydrides, such as, for example, lithium boranate, lithium hydridoborates, sodium hydridoboranates, boranes, sodium hydridoaluminates, lithium hydridoaluminates or tin hydrides, are particularly suitable for this. Lithium hydridoborates, such as, for example, lithium hydrido-triethyl-borate or lithium hydrido-tris(1-methylpropyl)borate, or sodium borhydride are particularly preferably employed.

Suitable solvents are the customary inert organic solvents used in reductions with hydrides. These are preferably ethers, such as diethyl ether and tetrahydrofuran. The reduction is carried out by a method analogous to known methods [W. Friedrichsen in Houben-Weyl, "Methoden der organischen Chemie" ("Methods of Organic Chemistry") VIII/1b, 145 et seq; and H. C. Brown, S. Krishnamurthy, Chem. Commun. 1972, 868].

The compound (IIa) can also be epimerised by a process analogous to other known processes, such as are described, for example, by O. Mitsunobu in Synthesis 1981, 1.

The preparation of II can be illustrated by the following equation:

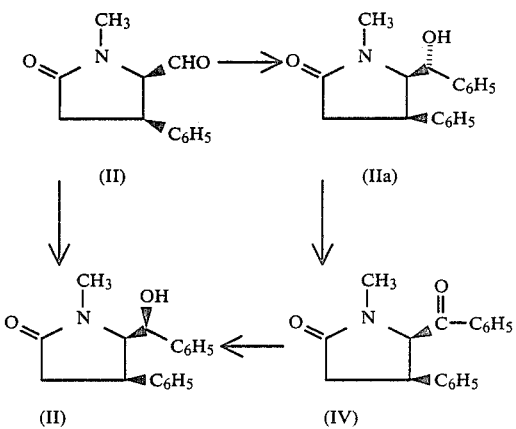

If the readily accessible phenyl-magnesium bromide is used as the organometallic reagent, almost exclusively the "incorrectly" configurated IIa is formed, and is epimerised to the "correctly" configurated II in the manner described.

The present invention also relates to the new compounds of the formulae IIa, IV and III.

The aldehyde of the formula III can be prepared in accordance with the following equation:

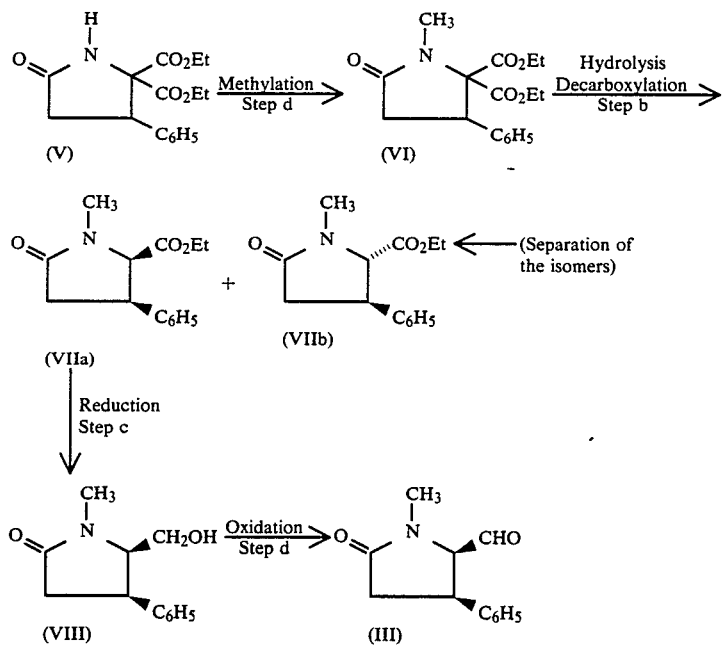

According to this equation, 5,5-diethoxycarbonyl-4-phenylpyrrolidin-2-one (V) is methylated in step a with a methylating agent, such as, for example, methyl bromide, methyl iodide, methyl p-toluenesulphonate, diazomethane or dimethyl sulphate, if appropriate in the presence of a base, such as sodium, sodium hydride, sodium amide, butyl-lithium or lithium diisopropylamide, in suitable solvents, such as diethyl ether, tetrahydrofuran, dimethylformamide or hexamethylphosphoric acid triamide, at temperatures from −20° to +80° C., preferably from 0° C. to +40° C. Methylation with methyl iodide in dimethylformamide is especially suitable. It has proved advantageous here to use sodium hydride as the base. The reaction is carried out and the product is worked up by customary methods familiar to the expert.

In step b, 5,5-diethoxycarbonyl-1-methyl-4-phenyl-pyrrolidin-2-one (VI) is hydrolyzed and decarboxylated by a process analogous to that described by P. Pachaly in Chem. Ber. 104, (2), 412–39 (1971), a mixture of the isomers VIIa and VIIb being obtained. After separation of the cis/trans isomers VIIa and b by recrystallization or chromatography, VIIa is reduced to (±)4(R*),5(R*)-5-hydroxymethyl-1-methyl-4-phenyl-pyrrolidin-2-one (VIII) (step c).

The reduction of VIIa to VIII is carried out by the same method and under the same conditions as have already been described for the reduction of IV to II.

The oxidation of VIII to III (step d) is carried out by the same method and under the same conditions as have already been described for the oxidation of IIa to IV.

The starting compound V is known from the literature [G. H. Cocolas, W. H. Hartung, J. Am. Chem. Soc. 79, 5203 (1957); and F. Zymalkowski, P. Pachaly, Chem. Ber. 100, 1137 (1967)].

The overall synthesis of clausenamide with all the new intermediate products is illustrated in the following equation:

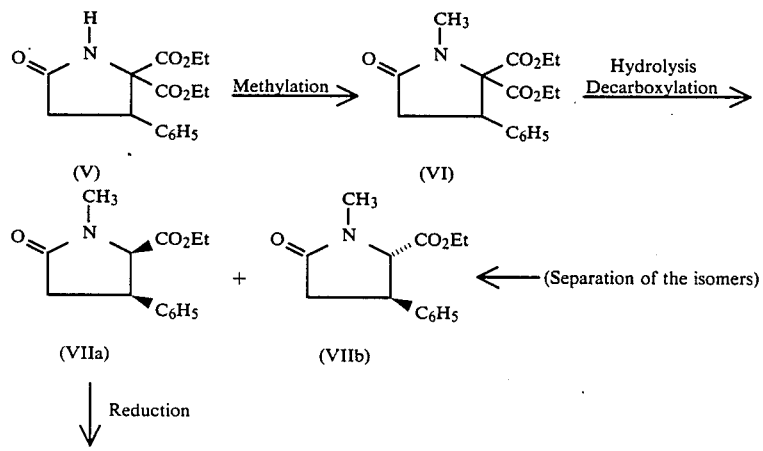

-continued

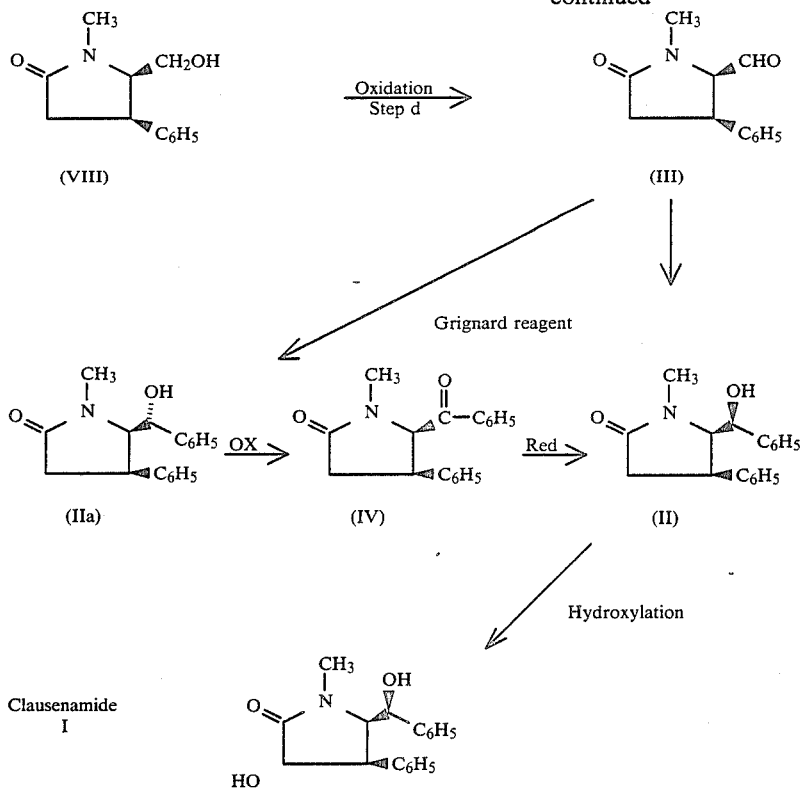

PREPARATION EXAMPLES

Example 1

(±) 5,5-Diethoxycarbonyl-4-phenylpyrrolidin-2-one

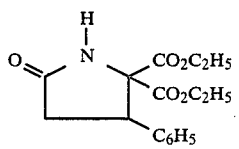

A solution of 18 g (0.8 gram atoms) of sodium in 400 ml of absolute ethanol was added dropwise to a suspension of 432 g (2 moles) of diethyl acetamidomalonate in 1.6 l of absolute ethanol at room temperature under an $N_2$ atmosphere. 564 g (3.2 moles) of ethyl cinnamate were slowly added and the mixture was then heated at the boiling point for 24 hours.

For working up, the mixture was allowed to come to room temperature, 2.5 l of chloroform were added and the mixture was neutralized with acetic acid. It was washed thoroughly with water (5×in each case 500 ml), dried over $MgSO_4$ and concentrated on a rotary evaporator. The oily residue was dissolved in a little acetone, hexane was added until crystallization occurred, and further hexane was then added until no further cloudiness was to be observed at the dropwise addition point. Filtration with suction gave 398 g (54%) of the title compound of melting point 97°–99° C. Chromatography of the mother liquor (toluene/ethyl acetate) gave a further 85 g (14%) of the title compound, total yield 413 g (68%).

IR(KBr): $\nu = 1770$ (ester), 1700 (amide)

$^1$H-NMR (300 MHz, $CDCl_3$): $\delta = 0.84$ and 1.28 (in each case t, $J = 7.5$ Hz; 6H, $CH_2\underline{CH_3}$); ABX signal: $\delta_A = 2.63$, $\delta_B = 2.96$ ($J_{AB} = 17.3$ Hz, $J_{AX} = 6$ Hz, $J_{BX} = 9$ Hz; 2H, C(3)-H); 3.66 and 3.71 (in each case m, 2H, cis-$CH_2CH_3$); 4.28 (m, 2H, trans-$CH_2CH_3$); 4.39 (dd, $J_{AX} = 6$ Hz, $J_{BX} = 9$ Hz, 1H, C(4)-H); 6.95 (br, 1H, NH); and 7.47 (br, 5H, $C_6H_5$).

EXAMPLE 2

(±) 5,5-Diethoxycarbonyl-1-methyl-4-phenyl-pyrrolidin-2-one

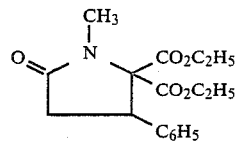

A solution of 100 g (0.33 mole) of (±) 5,5-diethoxycarbonyl-4-phenylpyrrolidin-2-one in 500 ml of absolute dimethylformamide was added dropwise to a suspension of 9.64 g (0.36 mole) of sodium hydride in 200 ml of absolute dimethylformamide at room temperature under an $N_2$ atmosphere. The mixture was subsequently stirred at room temperature until the evolution of gas had ended, a solution of 93.7 g (0.66 mole) of methyl iodide in 50 ml of absolute dimethylformamide was then added and the mixture was stirred at room temperature until all the starting material had reacted (about 1 hour, thin layer chromatography check). The reaction mixture was poured into 2 l of buffer solution, pH=7, and extracted five times with 600 ml of diethyl ether each time. Drying of the organic extracts ($MgSO_4$) and stripping off of the solvent in vacuo gave 105 g (99.6%) of the title compound (95% pure according to the ¹H-NMR spectrum), which was further reacted directly. A sample was distilled in a bulb tube (boiling point$_{0.5}$: 240° C.) for analysis, $R_f$: 0.36 (toluene/ethyl acetate: 2/1), IR (film): $\nu = 1735$ (ester), 1700 (amide)

¹H-NMR (500 MHz, CDCl$_3$): $\delta = 0.9$ and 1.33 (in each case t, J=7.5 Hz; 6H, CH$_2$CH$_3$); ABX signal: $\delta_A=2.66$, $\delta_B=3.0$ ($J_{AB}=18$ Hz, $J_{AB}=6$ Hz, $J_{BX}=8.3$ Hz; 2H, C(3)-H); 3.06 (s; 3H, N-CH$_3$); 3.62 and 3.79 (in each case m, 2H, cis-CH$_2$CH$_3$); 4.31 (m, 3H, trans-CH$_2$CH$_3$) and C(4)-H); and 7.26 (m, 5H, C$_6$H$_5$).

EXAMPLE 3

(±)4(R*),5(R*) [I] and
±4(R*),5(S*)-5-ethoxycarbonyl-1-methyl 4-phenylpyrrolidin-2-one [II]

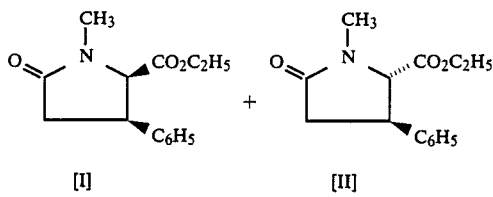

49.5 g (0.156 mole) of barium hydroxide octahydrate are heated in 483 ml of distilled water at 70° C. until an almost clear solution is formed. A solution of 100 g (0.313 mole) of (±)5,5-diethoxycarbonyl-1-methyl-4-phenylpyrrolidin-2-one in 724 ml of ethanol was added (clear solution) and the mixture was subsequently stirred at 70° C. for 20 minutes until the starting material had reacted completely (about 20 minutes, thin layer chromatography check). The mixture was cooled and acidified to pH=1-2, while cooling with ice, and the ethanol was stripped off in vacuo (bath temperature 30°-40° C.). The solid was filtered off with suction and aqueous phase was extracted, with addition of sodium chloride, 3 times with 200 ml of ethyl acetate each time. Drying and stripping off of the solvent gave a residue which was combined with the solid obtained above, and the mixture was dried in a desiccator over P$_4$O$_{10}$ under a high vacuum for 24 hours. The solid was then heated to 170° C. in an oil bath, while stirring thoroughly, until the evolution of gas had ended (5-10 minutes). Cooling and flash chromatography (cyclohexane/ethyl acetate=1/1, finally with ethyl acetate) gave 39.3 g (50.7%) of [I] with $R_f=0.10$ and 19.6 g (25.3%) of [II] with $R_f=0.20$ (in each case in cyclohexane/ethyl acetate 1/1).

IR(KBr): $\delta = 1736$, 1690 cm$^{-1}$

¹H-NMR (200 MHz, CDCl$_3$): [I] $\delta = 0.83$ (t, J=7.5 Hz; 3H, CH$_2$CH$_3$) ABX signal: $\delta_A=2.67$, $\delta_B$2.95 ($J_{AB}=17.5$ Hz, $J_{AX}=9$ Hz, $J_{BX}=10$ Hz, 2H, C(3)-H), 2.87 (s, 3H, N-CH$_3$), 3.75 (m, 2H, CH$_2$CH$_3$); 3.91 (q, J=9-10 Hz, 1H, C(4)-H), 4.36 (d, J=9 Hz, 1H, C(5)-H), 7.28 (m, 5H, C$_6$H$_5$).

[II] $\delta = 1.30$ (t, J=7.5 Hz, 3H, CH$_2$CH$_3$); ABX signal: $\delta_A=2.54$, $\delta_B=2.82$ ($J_{AB}=18.5$ Hz, $J_{AX}=5$ Hz, $J_{BX}=9$ Hz, 2H, C(3)-H), 3.80 (s, 3H, N-CH$_3$), 3.53 (ddd, J=9 Hz, J=5 Hz, J=4 Hz, 1H, C(4)-H), 4.07 (d, J=4 Hz, 1H, C(5)-H), 4.27 (m, 2H, CH$_2$—CH$_3$) 7.3 (m, 5H, C$_6$H$_5$).

Example 4

(±)4(R*),5(R*)-5-Hydroxymethyl-1-methyl-4-phenyl-pyrrolidin-2-one

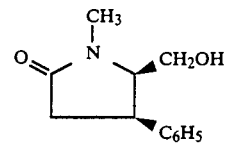

0.317 mole of LiB(Et)$_3$H (as in 1M solution in tetrahydrofuran, 316.9 ml) was added dropwise to a solution of 39.2 g (0.159 mole) of cis-4(R*),5(R*)-5-ethoxycarbonyl-1-methyl-4-phenylpyrrolidin-2-one in 390 ml of absolute tetrahydrofuran at $-15°$ to 20° C. under an N$_2$ atmosphere.

The reaction mixture was subsequently stirred at 0° C. for 1 hour, poured into about 200 ml of ice-cold 2N hydrochloric acid and extracted twice with 200 ml of ethyl acetate each time. The aqueous phase was saturated with sodium chloride and extracted twice more with 200 ml of ethyl acetate each time. The collected organic extracts were washed with a little water, dried over MgSO$_4$ and concentrated on a rotary evaporator. The residue was made to crystallize with a little ether and the product was then precipitated with pentane until no further cloudiness was to be observed at the dropwise addition point. After filtration with suction and drying, 29.1 g (89.2%) of the title compound of melting point 93°-95° C. were obtained.

IR(KBr): $\nu = 3324$, 1687 cm$^{-1}$

¹H-NMR (300 MHz, CDCl$_3$): $\delta$ = AB-part of ABM system, $\delta_A=2.59$, $\delta_B=2.97$ (in each case dd, $J_{AB}=15$ Hz, $J_{AM}=7.5$ Hz, $J_{BM}=9$ Hz, 2H, C(3)-H); 2.97 (s, 3H, N—CH$_3$) AB-part of ABM system, $\delta_A=3.36$, $\delta_B=3.62$ (in each case dd, $J_{AB}=11.2$ Hz, $J_{AM}=J_{BM}=3$ Hz, 2H, C(7)-H; 3.72-3.85 (m, 2H, C(4)-H, C(5)-H); 7.32 (m, 5H, C$_6$H$_5$).

Example 5

4(R*),5(R*)-5-Formyl-1-methyl-4-phenylpyrrolidin-2-one

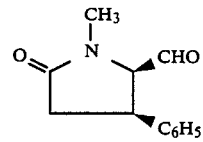

A solution of 29.7 ml of trifluoroacetic anhydride in 56 ml of absolute methylene chloride was added dropwise at $-60°$ C. to a solution of 19.9 ml (0.28 mole) of absolute dimethyl-sulphoxide in 140 ml of absolute methylene chloride under an N$_2$ atmosphere in the course of 10 minutes. The mixture was stirred at this temperature for 15 minutes and a solution of 28.8 g (0.140 mole) of 4(R*),5(R*)-5-hydroxymethyl-1-methyl-4-phenylpyrrolidin-2-one in 250 ml of methylene chloride was added dropwise such that the temperature did not exceed $-60°$ C. The mixture was subsequently stirred at $-60°$ C. for 90 minutes, warmed briefly to $-30°$ C. (5-10 minutes) and cooled again to $-60°$ C. 56 ml of absolute triethylamine were slowly added at this temperature and the mixture was stirred at $-60°$ C. for 30 minutes and warmed to room temperature. 600 ml of water were added, the phases were separated and the aqueous phase was extracted three times with 250 ml of methylene chloride each time. The collected organic extracts were washed twice with 300 ml of water each time, dried over magnesium sulphate and extracted. 28.3 g (100%) of the title compound with $R_f=0.25$ (ethyl acetate) (91% pure according to the $^1$H-NMR spectrum) were obtained. The crude product thus obtained was further reacted directly, after drying (24 hours, high vacuum).

IR (CHCl$_3$): $\nu=1734$, 1689 cm$^{-1}$ $^1$H-NMR (300 MHz, CDCl$_3$): $\delta$ 2.79 (dd, J=5.3 Hz, J=9.7 Hz, 2H, C(3)-H); 2.91 (s, 3H, N—CH$_3$); 4.02 (q, J=9.7 Hz, 1H, C(4)-H); 4.30 (dd, J=1 Hz, J=9.7 Hz, 1H, C(5)-H); 7.3 (m, 5H, C$_6$H$_5$), 9.17 (d, J=1 Hz, 1H, CHO).

Example 6

4(R*),5(R*),7(R*)-5-α-Hydroxybenzyl-1-methyl-4-phenylpyrrolidin-2-one

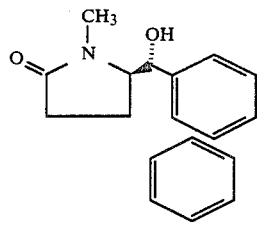

A solution of 24.8 g (16.7 ml, 0.156 mole) of bromobenzene in 44 ml of absolute tetrahydrofuran was added dropwise to 3.84 g of Mg filings under N$_2$ such that the tetrahydrofuran simmered. 100 ml of absolute tetrahydrofuran were then added and the mixture was heated at the boiling point under reflux until all the magnesium had dissolved (1–2 hours).

The mixture was cooled to 0° C. and a solution of 24.7 g (0.12 mole) of 4(R*),5(R*)-5-formyl-1-methyl-4-phenylpyrrolidin-2-one in 250 ml of absolute tetrahydrofuran was added dropwise, with vigorous stirring, such that the temperature did not exceed 5° C. If necessary, absolute tetrahydrofuran had to be added for better stirrability. The reaction mixture was then stirred at 0°–5° C. for 1 hour, poured onto 350 ml of 0.5N HCl-ice and extracted four times with 300 ml of ethyl acetate each time and twice with 300 ml of methylene chloride each time. The collected ethyl acetate and methylene chloride extracts were washed (separatelyl) twice with 200 ml of water each time, combined and dried over magnesium sulphate. The residue which remained after stripping off of the solvent (in vacuo) was triturated with 100 ml of ether until crystallization occurred. 500 ml of pentane were then slowly added and the mixture was left to stand overnight in a refrigerator. Filtering off of the solid with suction gave 25 g (74.3%) of the title compound of melting point: 210°–212° C.

For analysis, the product was recrystallized from acetone (melting point: 214°–5° C.).

IR(KBr) $\nu=3362$ (br), 1654 cm$^{-1}$ $^1$H-NMR (300 NHz, d$_6$-DMSO): $\delta=2.21$ (s, 3H, NCH$_3$); 2.24 (dd, A-part of ABM system, $J_{AB}=15.7$ Hz, $J_{AM}=9.4$ Hz, 1H, cis-C(3)-H); 3.05 (dd, B-part of ABM system, $J_{BM}=12.7$ Hz, 1H, trans-C(3)-H); 3.80 (dt, M-part of ABM system, $J_{AM}=8.5$ Hz, $J_{AB}=12.7$ Hz, $J_{4,5}=8.5$ Hz, 1H, C(4)-H); 4.15 (dd, J=8.5 Hz, J=1 Hz, 1H, C(5)-H); 4.26 (dd, J=6 Hz, J=1 Hz, 1H, C(7)-H); 5.35 (d, J=6 Hz, 1H, OH); 7.15–7.5 (m, 10H, C$_6$H$_5$).

Example 7

4(R*),5(R*)-5-Benzoyl-1-methyl-4-phenylpyrrolidin-2-one

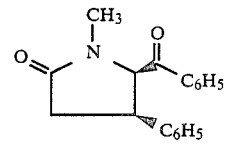

A solution of 18 ml of trifluoroacetic anhydride in 34 ml of absolute methylene chloride was added dropwise to a solution of 12.24 ml (0.171 mole) of absolute dimethylsulphoxide in 87 ml of absolute methylene chloride at $-60°$ C. under an N$_2$ atmosphere in the course of 10 minutes. The mixture was subsequently stirred at this temperature for 15 minutes and a solution of 24 g (0.085 mol) of 4(R*),5(R*),7(R*)-5-α-hydroxybenzyl-1-methyl-4-phenylpyrrolidin-2-one in about 700 ml of absolute methylene chloride was added dropwise such that the temperature did not exceed $-60°$ C. The mixture was subsequently stirred at $-60°$ C. for 90 minutes, warmed briefly to $-30°$ C. (9–10 minutes) and cooled again to $-60°$ C. 34.2 ml of triethylamine were slowly added at this temperature and the mixture was stirred at $-60°$ C. for 20 minutes and warmed to room temperature. 370 ml of water were added, the phases were separated and the aqueous phase was extracted three times with 250 ml of methylene chloride each time. The combined organic extracts were washed twice with 300 ml of water each time, dried over magnesium sulphate and concentrated on a rotary evaporator. The residue was evaporated in a rotary evaporator twice with 200 ml of ether each time. 23.5 g (100%) of the title compound were obtained as a solid of melting point: 115°–116° C. The crude product, which was pure according to the $^1$H-NMR spectrum, was further reacted directly.

For analysis, a sample was chromatographed over silica gel with ethyl acetate ($R_f=0.25$), melting point: 121°–2° C.

IR(KBr): $\nu=1695$, 1682 cm$^{-1}$ $^1$H-NMR (300 MHz, CDCl$_3$) $\delta=2.78$ and 2.91 (AB-part of ABM spectrum, $J_{AB}=16.5$ Hz, $J_{AM}=J_{BM}=8.3$ Hz, 2H, C(3)-H); 2.88 (s, 3H, N-CH$_3$); 4.02 (q, J=8.3 Hz, 1H, C(4)-H); 5.42 (d, J=8.3 Hz, 1H, C(5)-H); 7.0, 7.21, 7.59 and 7.50 (in each case m, 10H, C$_6$H$_5$).

Example 8

4(R*),5(R*),7(S*)-5-α-Hydroxybenzyl-1-methyl-4-phenylpyrrolidin-2-one

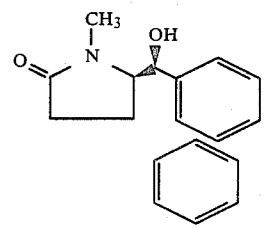

83 mmol of LiB(Et)$_3$H (83 ml of a 1M solution in tetrahydrofuran) were added dropwise to a solution of 23 g (82.3 mmol) of 4(R*),5(R*)-5-benzoyl-1-methyl-4- phenylpyrrolidin-2-one in 200 to 270 ml of absolute tetrahydrofuran at −15° to −20° C. under an $N_2$ atmosphere. The reaction mixture was subsequently stirred at 0° C. for 1 hour, poured into 100 ml of ice-cold 1N HCl and extracted twice with 200 ml of ethyl acetate each time. The aqueous phase was saturated with sodium chloride and extracted twice more with 200 ml of ethyl acetate each time. The combined organic extracts were dried over $MgSO_4$ and concentrated on a rotary evaporator. The residue was dissolved in methylene chloride and washed twice with 100 ml of water each time. The organic phase was dried ($MgSO_4$) and concentrated on a rotary evaporator. The residue was made to crystallize with 100 ml of ether, and pentane was then slowly added, with stirring, until no further cloudiness was to be observed at the dropwise addition point. The precipitate was filtered off with suction and dried. 16.6 g (72%) of the title compound of melting point: 189°–195° C. were obtained.

The product is 95% pure according to $^1$H-NMR and was further reacted directly.

For analysis, the product was recrystallised from acetone (melting point: 197°–8° C.).

IR(KBr): $\nu=3251, 1692$ cm$^{-1}$ $^1$H-NMR (300 MHz, DMSO): $\delta=1.97$ and 2.05 (ABM signal, $J_{AB}=13.5$ Hz, $J_{AM}=8.2$ Hz, $J_{BM}=13$ Hz, 2H, C(3)-H); 2.91 (s, 3H, N-CH$_3$); 3.82 (dt, $J_{AM}=J_{4.5}=8.2$ Hz, $J_{BM}=13$ Hz, 1H, C(4)-H); 4.27 (dd, $J=8.2$ Hz, $J=1.5$ Hz, 1H, C(5); 4.65 (dd, $J=1.5$ Hz, $J=3.5$ Hz, 1H, C(7)-H); 5.34 (d, $J=3.5$ Hz, 1H, OH); 6.70, 7.11 and 7.25 (in each case m, 10H, C$_6$H$_5$).

Example 9

3(S*),4(R*),5(R*),7(S*)-3-Hydroxy-5-α-hydroxybenzyl-1-methyl-4-phenylpyrrolidin-2-one (clausenamide)

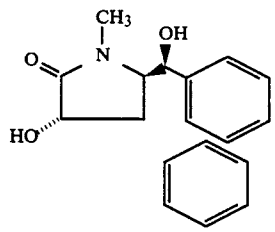

A solution of 17.7 g (62.0 mmol) of 4(R*),5(R*),7(S*)-5-α-hydroxybenzyl-1-methyl-4-phenylpyrrolidin-2-one in 490 ml of absolute tetrahydrofuran and 130 ml of absolute hexamethylphosphoric acid triamide was introduced into a flask which had been heated thoroughly in vacuo and flushed with pure nitrogen, and the solution was cooled to −70° C. A solution of 0.152 mole of lithium diisopropylamide in 180 ml of absolute tetrahydrofuran/hexane (prepared from 22.1 ml of diisopropylamine in 80 ml of tetrahydrofuran by addition of 103 ml of a 1.5N solution of n-butyl-lithium in hexane at −20° C. to 0° C.) was added dropwise at this temperature. The mixture was subsequently stirred at −70° C. to −60° C. for 1 hour, 5.3 ml of freshly distilled trimethyl phosphite (dissolved in a little absolute tetrahydrofuran) were added and absolute oxygen (dried over $H_2SO_4$ and $P_4O_{10}$) was passed in (50–100 ml/minute). As soon as the product/starting material ratio no longer changed (2–3 hours) according to thin layer chromatography check (SiO$_2$; ethyl acetate/MeOH: 2/1; R$_f$=0.3 for the title compound, R$_f$=0.37 for the starting compound, staining with molybdatophosphoric acid spray reagent), the mixture was poured onto 600 ml of 0.5N HCl, while cooling with ice, and if appropriate acidified to pH 3 to 4.

The phases were separated and the aqueous phase was extracted four times with 300 ml of ethyl acetate each time. The combined organic extracts were washed three times with 300 ml of water each time, dried over $MgSO_4$ and concentrated on a rotary evaporator. The residue was taken up in 50–100 ml of ether, the mixture was stirred until crystallization started and pentane was slowly added, with stirring, until no further cloudiness was to be observed at the dropwise addition point. The mixture was left to stand overnight in a refrigerator and filtered with suction. about 17 g of a crude solid which, in addition to the title compound, contained about 35–40% of starting material were obtained. For purification, the product is recrystallized twice from methanol. The title compound is then obtained in a purity of about 95%. Chromatography over aluminum oxide (neutral) proceeds without losses and with recovery of the pure starting material. For this, the crude product is absorbed onto silica gel (dissolving in MeOH under the influence of heat, addition of 5 parts by weight of silica gel, concentration on a rotary evaporator and evaporation on a rotary evaporator several times with ethyl acetate until an MeOH-free product as dry as dust results). The adsorbate is introduced onto a column containing Al$_2$O$_3$ (neutral, 50 parts by weight) and the starting material is eluted first with ethyl acetate (flash chromatography, check by thin layer chromatography and analytical high performance liquid chromatography). The title compound is then eluted with ethyl acetate/methanol mixtures (40/1, 20/1 and then 10/1). 8.6 g (46.1%) of the title compound of melting point: 236°–7.5° C. (authentic clausenamide: 236°–7° C.) and a purity of about 98% (according to $^1$H-NMR, contains about 2% of starting material) were obtained. It was possible to recover 5 g of the pure starting material.

IR(KBr): $\nu=3402, 3321, 1689$ cm$^{-1}$ $^1$H-NMR (300 MHz, DMSO): $\delta=3.01$ (s, 3H, N-CH$_3$); 3.50 (dd, J=8 Hz, J=10.5 Hz, 1M, C(4)-H); 3.82 (dd, J=10 Hz, J=7 Hz, 1H, C(3)-H); 4.30 (dd, J=8 Hz, J=2 Hz, 1H, C(5)-H); 4.65 (dd, J=2 Hz, J=3 Hz, 1H, C(7)-H), 5.39 (d, J=7 Hz, 1H, C(3)-OH); 5.45 (d, J=3 Hz, 1H, C(7)-OH; 6.61–6.64 (m, 2H, aromatic H) and 7.03–7.28 (m, 8H, aromatic H).

What is claimed is:

1. (±)4(R*),5(R*),7(S*)-5-α-Hydroxybenzyl-1-methyl-4-phenylpyrrolidin-2-one of the formula

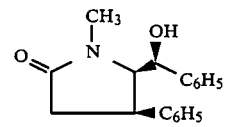

2. (±)4(R*),5(R*)-5-Formyl-1-methyl-4-phenyl-pyrrolidine-2-one of the formula

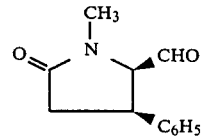

3. (±)4(R*),5(R*)-5-Benzoyl-1-methyl-4-phenylpyrrolidin-2-one of the formula
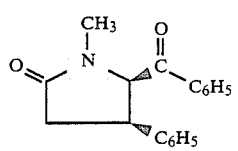
4. (±)4(R*),5(R*)-5-Hydroxymethyl-1-methyl-4-phenylpyrrolidin-2-one of the formula
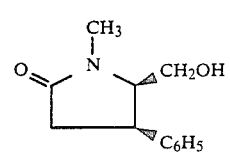
* * * * *